(12) United States Patent
Fergason

(10) Patent No.: US 7,342,210 B2
(45) Date of Patent: *Mar. 11, 2008

(54) REMOTE CONTROL FOR AUTO-DARKENING LENS SYSTEMS AND METHOD

(75) Inventor: John D. Fergason, Cupertino, CA (US)

(73) Assignee: LightSwitch Safety Systems, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/898,297

(22) Filed: Jul. 23, 2004

(65) Prior Publication Data

US 2005/0017152 A1   Jan. 27, 2005

Related U.S. Application Data

(60) Provisional application No. 60/489,345, filed on Jul. 23, 2003.

(51) Int. Cl.
G01J 1/44 (2006.01)
H01J 40/14 (2006.01)
H01J 1/56 (2006.01)
B01D 5/34 (2006.01)

(52) U.S. Cl. .............. 250/206; 250/215; 250/229; 2/8; 2/427; 349/14; 349/16; 396/263

(58) Field of Classification Search ............ 250/205, 250/206, 215, 229; 359/601; 349/14, 16; 2/8, 906; 396/263, 297; 367/198
See application file for complete search history.

(56) References Cited

U.S. PATENT DOCUMENTS 3,731,986 A   5/1973   Fergason 3,881,809 A   5/1975   Fergason et al.
4,039,254 A   8/1977   Harsch
RE29,684 E   6/1978   Gordon (Continued)

FOREIGN PATENT DOCUMENTS

EP   0 678 288 A2   4/1995

(Continued)

OTHER PUBLICATIONS

International Search Report relating to application PCT/US2004/023743, dated mailed Mar. 12, 2004.

Primary Examiner—Patrick J. Lee
(74) Attorney, Agent, or Firm—Renner, Otto, Boisselle & Sklar, LLP

(57) ABSTRACT

A wireless remote control is provided for an auto-darkening lens (ADL) system used in a welding helmet, respirator system or other device to control or to adjust settings of an ADL of a controllable light shutter. A display system facilitates providing information indicating the operative settings and/or conditions of the controllable light shutter. A wired remote control for controlling or adjusting an ADL also uses a display system with indicators to indicate the operative settings and/or conditions of the ADL. The display may include a number of indicators, an alpha-numeric display, a heads-up display or other display. The display may include discrete indicators in the peripheral field of view of one eye of a user a controllable. The invention also includes methods of using a remote control for an ADL and of making an ADL to provide for future use of a wireless remote control.

43 Claims, 8 Drawing Sheets

U.S. PATENT DOCUMENTS

| | | |
|---|---|---|
| 4,385,806 A | 5/1983 | Fergason |
| 4,436,376 A | 3/1984 | Fergason |
| 4,540,243 A | 9/1985 | Fergason |
| 4,582,396 A | 4/1986 | Bos et al. |
| 4,679,255 A * | 7/1987 | Kuhlman ............... 2/8.3 |
| RE32,521 E | 10/1987 | Fergason |
| 5,074,647 A | 12/1991 | Fergason et al. |
| 5,208,688 A | 5/1993 | Fergason et al. |
| 5,248,880 A | 9/1993 | Fergason |
| 5,252,817 A | 10/1993 | Fergason et al. |
| 5,347,383 A | 9/1994 | Fergason |
| 5,510,609 A | 4/1996 | Ackermann |
| 5,519,522 A | 5/1996 | Fergason |
| 5,751,258 A | 5/1998 | Fergason et al. |
| 5,959,705 A | 9/1999 | Fergason |
| 6,067,129 A * | 5/2000 | Fergason ............... 349/14 |
| 6,070,264 A * | 6/2000 | Hamilton et al. ............ 2/8 |
| 6,242,711 B1 | 6/2001 | Cooper |
| 6,369,952 B1 | 4/2002 | Rallison et al. |
| 6,710,298 B2 * | 3/2004 | Eriksson ............ 219/130.01 |
| 7,005,624 B2 * | 2/2006 | Hamilton ............... 250/205 |
| 7,150,047 B2 * | 12/2006 | Fergason ............... 2/8.1 |
| 2003/0206491 A1* | 11/2003 | Pacheco et al. ........... 367/198 |
| 2005/0002083 A1* | 1/2005 | Fergason ............... 359/276 |

FOREIGN PATENT DOCUMENTS

WO    WO 02/49554 A1    6/2002

* cited by examiner

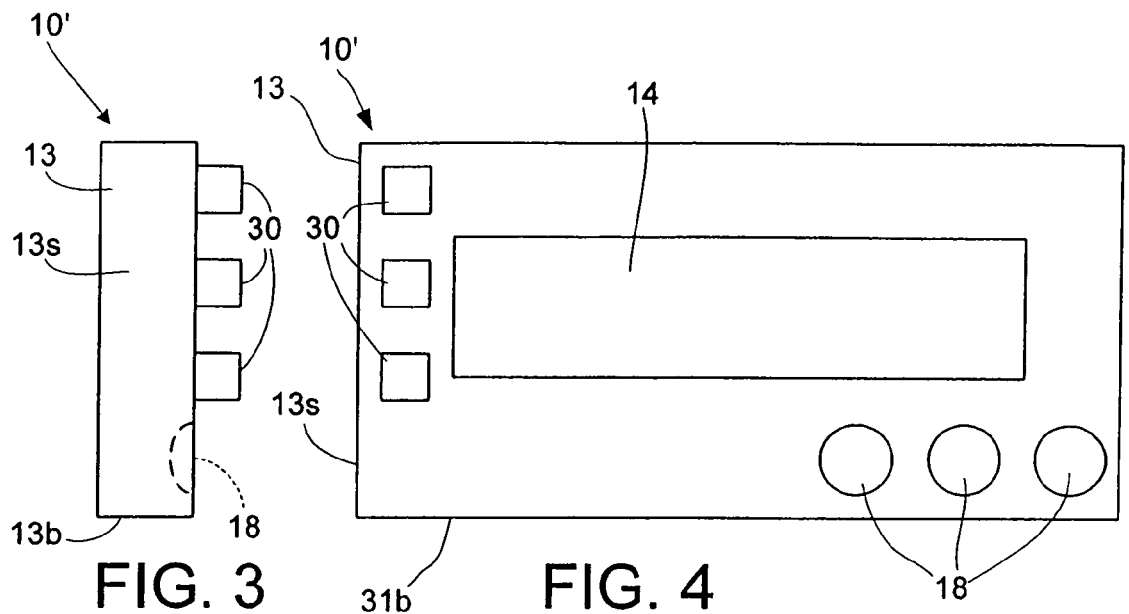
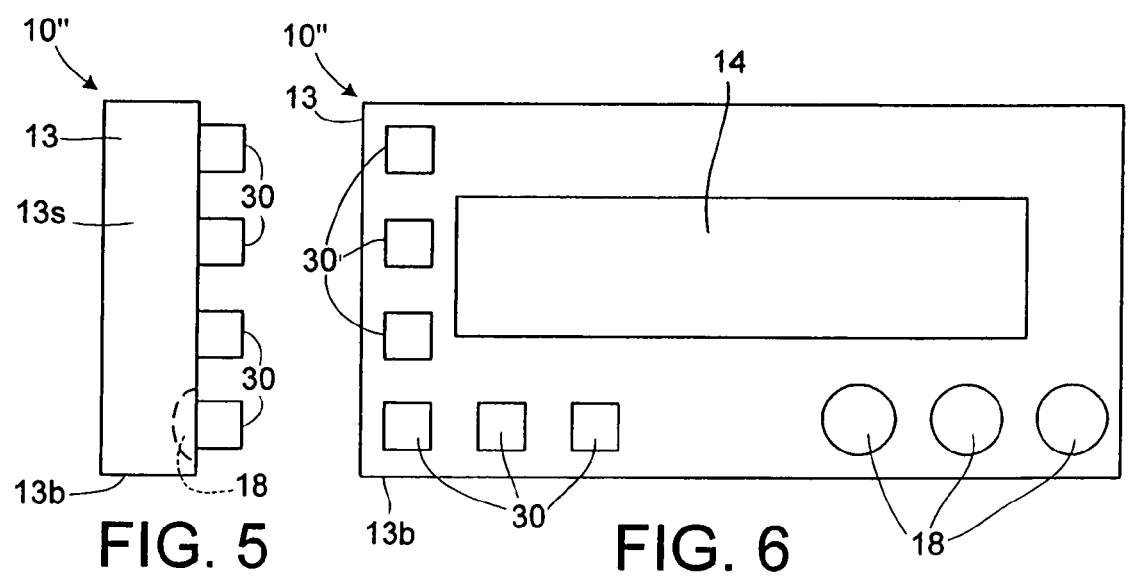

REMOTE CONTROL FOR AUTO-DARKENING LENS SYSTEMS AND METHOD

CROSS-REFERENCE TO RELATED APPLICATION

This application claims the benefit of U.S. Provisional Application Ser. No. 60/489,345, filed Jul. 23, 2003, the entire disclosure of which are incorporated by this reference.

TECHNICAL FIELD

The present invention relates generally, as indicated, to a remote control for auto-darkening lens (ADL) systems and method.

BACKGROUND

In the field of welding and in other fields, to protect the eyes of a person automatically darkening lens devices, sometimes referred to as auto-darkening lenses, have been used. Auto-darkening lenses may have, for example, a light shutter that is controllable to control the amount of light transmitted through it, and a light sensitive device and associated control and/or operating circuitry to sense the light that is incident on the light shutter and in response to the sensed light to control the light transmitting characteristics of the shutter. The controllable shutters may be used in welding helmets, respirator helmets and systems, safety eye glasses, regular eye glasses, goggles, and other devices used to protect the eyes of a wearer or user.

In systems that use auto-darkening lenses, such as welding helmets, respirator helmets and systems, safety eye glasses, regular eye glasses, goggles, and other devices used to protect the eyes of a wearer or user, it may be inconvenient or even undesirable to remove the system, e.g., a respirator helmet or welding helmet, to make adjustments to shade number setting, sensitivity, and/or other adjustments. Indeed, in a harsh environment a person may not want to remove a respirator helmet in which an air supply is provided and it also may be difficult to remove the helmet. For example, it is difficult to remove and to reinstall the helmet of a powered air respirator. However, for various reasons, after the system is put on, e.g., a helmet is placed on a user's head, it may be desirable to make adjustments to the operation of the controllable shutter, its operating circuitry, etc.

In prior welding helmets and respirator helmet systems, for example, knobs have been provided on the outside of the helmet system to allow the user to make adjustments while the helmet system is being worn. However, to do this it is necessary to place a hole in the helmet body, for example, to provide for connections with circuitry within the helmet near the user's face. Making the hole is difficult; making the hole may damage the helmet; making the hole may reduce the sealed integrity of a respirator helmet that is intended to protect the user from the external environment. For these reasons, too, it is difficult and may be undesirable to retrofit an existing welding helmet or the like with ability to make adjustments to controls for the auto-darkening lens while the helmet is being worn.

Accordingly, there is a need to facilitate making such adjustments without removing the system in which the auto-darkening lens is used, e.g., helmet, goggles, etc.

Also, users of prior helmets and associated auto-darkening lenses were unable easily to know the settings made by such external adjustment knobs. In the past manual feedback was used to convey to a user that a given setting was made, e.g., the user may know how far he or she turned a given knob; but manual feedback may not be possible or may be inaccurate, especially if a user is wearing welding gloves or the like.

Accordingly, there also is a need to indicate to the user the adjustments or settings made and/or other pertinent information to a welding helmet and/or the auto-darkening lens thereof without having to remove the helmet, etc.

Various light sensitive devices have been used in the past, such as, for example, photocells, photosensors, light sensors, light sensitive solid state devices, such as light sensitive or photosensitive diodes, photosensors, and other devices (collectively devices to sense light will be referred to herein by those terms and/or by other similar representative terms, all of which are considered equivalent).

In an exemplary auto-darkening lens or other systems in which it is desired automatically to control light transmission, a controllable shutter is controlled to respective dark and/or bright or clear states (or modes) and possibly to intermediate states therebetween. The shutter may be, for example, a liquid crystal shutter or some other shutter that controls light transmission, for example, without affecting image characteristics of light transmitted through the shutter. The operating circuitry operates the shutter to assume the respective states, and the light sensor senses light conditions and provides an input to the operating circuitry to operate the shutter in response to the sensed light conditions. The photosensor provides an output representative of that light. The light may be in the visible, ultraviolet, infrared, or some other spectrum range or combination of ranges.

In an exemplary auto-darkening lens the sensor is placed at the front of a support structure or housing in which the shutter is mounted or the sensor may be in the support structure (e.g., housing), which is provided with an access opening to allow light to reach the sensor. The location at which the sensor is mounted on or in the support structure may be selected to allow the light sensor to receive incident light that is representative of light, which impinges on the shutter. It is desirable that the intensity of the light incident on the sensor would be representative of the light incident on the shutter. In an auto-darkening lens or other controllable light shutter device used for welding it is desirable to detect light representing the occurrence of welding and to distinguish such light from ambient light.

In the description herein reference will be made to a lens (also sometimes referred to as "welding lens," "welding filter," "shutter," and the like, and to an automatically darkening lens (sometimes referred to as auto-darkening lens)) that is able to operate automatically to control transmission of light. The lens may be a light shutter type of a device that is able to control light transmission without distorting, or at least with relatively minimal distortion, of the light and the image characteristics carried by the light or represented by the light. Therefore, when a person looks through the lens, the image seen would be substantially the same as the image seen without the lens, except that the intensity of the light transmitted through the lens may be altered depending on the operative state of the lens. The lens may be used in a welding helmet, and the lens may be used in other types of devices, such as goggles, spectacles, face masks, e.g., for industry (such as in an industrial plant or to protect outdoor or indoor electrical workers), for dentistry to protect the face of a dentist in the operative, respirator systems, nuclear flash eye protection devices, and other types of helmets, etc. Such devices usually are employed to protect the face or the eyes of a person, as is known, for example, in the field of welding and in other fields, too. Further, the lenses may be used in various other places to protect workers from bright light that could present a risk of injury.

For the purposes of providing eye protection, usually a welding lens provides light blocking characteristics in the visible, infrared and/or ultraviolet wavelength ranges. The actual ranges may be determined by the components of the lens, the arrangement of those components, and so forth. One example of such a welding lens is U.S. Pat. No. 5,519,522. The lens assembly disclosed in that patent includes several liquid crystal cell light shutters, several plane polarizers, and a reflector or band pass filter, which is able to reflect ultraviolet and infrared electromagnetic energy and possibly also some electromagnetic energy in the visible wavelength range. The several liquid crystal cells, for example, may be birefringent liquid crystal cells sometimes referred to as surface mode liquid crystal cells or pi-cells.

As will be described further below, the present invention may be used in a variable optical transmission controlling device. The device is described in detail with respect to use in a welding helmet. However, it will be appreciated that the device may be employed in other environments and in other devices and systems for controlling transmission of electromagnetic energy broadly, and, in particular, optical transmission. As used herein with respect to one example, optical transmission means transmission of light, i.e., electromagnetic energy that is in the visible spectrum and also may include ultraviolet and infrared ranges. The features, concepts, and principles of the invention also may be used in connection with electromagnetic energy in other spectral ranges.

Examples of liquid crystal cells and shutters (the terms liquid crystal cell and liquid crystal shutter may be used interchangeably and equivalently herein unless context indicates or implies otherwise), lenses using them and drive circuits are described in U.S. Pat. Nos. 5,208,688, 5,252,817, 5,248,880, 5,347,383, and 5,074,647. In U.S. Pat. No. 5,074,647, several different types of variable polarizer liquid crystal devices are disclosed. Twisted nematic liquid crystal cells used in an automatic shutter for welding helmets are disclosed in U.S. Pat. Nos. 4,039,254 and Re. 29,684. Exemplary birefringent liquid crystal cells useful as light shutters in the present invention are disclosed in U.S. Pat. Nos. 4,385,806, 4,436,376, 4,540,243, 4,582,396, and Re. 32,521 and exemplary twisted nematic liquid crystal cells and displays are disclosed in U.S. Pat. Nos. 3,731,986 and 3,881,809. Another type of liquid crystal light control device is known as a dyed liquid crystal cell. Such a dyed cell usually includes nematic liquid crystal material and a pleochroic dye that absorbs or transmits light according to orientation of the dye molecules. As the dye molecules tend to assume an alignment that is relative to the alignment of the liquid crystal structure or directors, a solution of liquid crystal material and dye placed between a pair of plates will absorb or transmit light depending on the alignment of the liquid crystal material. Thus, the absorptive characteristics of the liquid crystal device can be controlled as a function of applied electric field.

As is disclosed in several of the above patents, the respective shutters may have one or more operational characteristics (sometimes referred to as modes or states). One example of such an operational characteristic is the shade number; this is the darkness level or value of the shutter when it is in the light blocking mode (dark state). Another exemplary operational characteristic is the delay time during which the shutter remains in a dark state after a condition calling for the dark state, such as detection of the bright light occurring during welding, has ceased or detection thereof has terminated or been interrupted. Still another operational characteristic is sensitivity of the detection circuit and/or shutter to incident light, for example, to distinguish between ambient conditions and the bright light condition occurring during a welding operation, and sensitivity also may refer to shutter response time or to the time required for the circuitry associated with the lens to detect a sharp increase in incident light (e.g., due to striking of the welding arc, etc.) and to switch the lens from the clear state to the dark state. Even another characteristic, which may be considered an operational characteristic, is the condition of the battery or other power source for the shutter, such as the amount of power remaining, operational time remaining until the power source becomes ineffective, etc. In the past various of the operational characteristics of such shutters have been adjustable or fixed.

Dynamic operational range or dynamic optical range is the operational range of the lens between the dark state and the clear state, e.g., the difference between the shade numbers of the dark state and the clear state.

An example of a "welding lens with integrated display and method" is disclosed in U.S. Pat. No. 6,067,129. In the invention disclosed therein the current operational characteristics of the shutter can be displayed and can be selectively changed by operating one or more switches. The switches may be flexible membrane switches, microswitches, or another type of switch.

The present invention is useful for eye protection by an automatic darkening light shutter in a helmet or goggle assembly or in another device, if desired. The switching mechanism for powering the light shutter on and off and/or for selecting operational characteristics may be an integral part of the light shutter and/or frame assembly or other component or portion thereof.

The light shutter, photosensor arrangement and/or control of the present invention may be used in a variety of embodiments and applications. The shutter is adjustable to control light, i.e., to increase or to decrease the amount of the incident light that is transmitted through the shutter. When welding is not occurring, for example, the shutter in a welding helmet may be substantially optically clear or transmissive or at least minimizes its attenuation of light. When welding is occurring, the shutter may be dark or closed to reduce the amount of light transmitted therethrough in order to protect the eyes of the person performing the welding and to maximize his or her viewing comfort. In both cases, though, the image characteristics of the light preferably remain intact. A photosensitive device may be used to sense the intensity of light impinging in the area of the shutter so as to provide an input to a drive circuit or operating circuitry for the shutter in order to control opening and closing thereof.

The disclosures of the patents identified herein are incorporated in their entirety by reference.

SUMMARY

An aspect of the present invention relates to an auto-darkening lens system including an auto-darkening lens, including a controllable light shutter, operating circuitry to control light transmitting characteristics of the controllable light shutter, and a wireless remote control to adjust at least one operating parameter of the auto-darkening lens.

Another aspect relates to an auto-darkening lens system including an auto-darkening lens, including a controllable light shutter, operating circuitry to control light transmitting characteristics of the controllable light shutter, a wired remote control to adjust at least one operating parameter of the auto-darkening lens, and indicators to indicate at least one of a setting and an operating condition of at least one of the auto-darkening lens and operating circuitry.

Another aspect relates to a wireless remote control for an auto-darkening lens including a mode selector to select an operational mode of an auto-darkening lens, a value selector to adjust the selected operational mode, and a transmitter to transmit signals to an auto-darkening lens.

Another aspect relates to a wired remote control for an auto-darkening lens including a mode selector to select an operational mode of an auto-darkening lens, a value selector to adjust the selected operational mode, a wired connection to an auto-darkening lens, and indicators to indicate at least one of a setting and an operating condition of at least one of the auto-darkening lens, mode selector and value selector.

Another aspect relates to a method of operating an auto-darkening lens including using a wireless remote control providing control inputs to an auto-darkening lens to adjust at least one operating mode thereof.

Another aspect relates to a method of operating an auto-darkening lens including using a wireless remote control providing control inputs to an auto-darkening lens to adjust at least one operating mode thereof, and displaying on the wireless remote control information indicating operational setting or operation of the auto-darkening lens.

Another aspect relates to a method of making an auto-darkening lens including preparing circuitry for operating a controllable light shutter of an auto-darkening lens, the preparing including preparing a receiver to receive wireless signals from a wireless remote control to adjust operation of such controllable shutter.

Another aspect relates to an auto-darkening lens system including an auto-darkening lens, including a controllable light shutter, operating circuitry to control light transmitting characteristics of the controllable light shutter, and a heads-up display to provide information concerning the auto-darkening lens in the area of the controllable light shutter of the auto-darkening lens.

An aspect of the invention relates to a remote control for adjusting one or more adjustable functions of an auto-darkening lens.

Another aspect of the invention relates to a method for remotely adjusting functions of an auto-darkening lens.

Another aspect relates to adjusting operation of an auto-darkening lens while the system in which it is used is worn by a user.

Another aspect relates to providing redundant controls for an auto-darkening lens and system using it.

Another aspect relates to providing redundant controls, one of which is dominant over the other, for an auto-darkening lens and system using it.

Another aspect relates to providing versatile controls for an auto-darkening lens and system using it.

Another aspect relates to the retrofitting of an auto-darkening lens in a standard system, e.g., welding helmet, respirator, goggles, etc., and providing external controls therefor.

Another aspect relates to facilitating the adding of a remote control adjustment for a system that uses an auto-darkening lens.

Another aspect relates to an auto-darkening lens with a heads-up display.

Another aspect relates to providing information to a user of an auto-darkening lens using a heads-up display.

Another aspect relates to an auto-darkening lens system including an auto-darkening lens, including a controllable light shutter, operating circuitry to control light transmitting characteristics of the controllable light shutter, and a remote control to adjust at least one operating parameter of the auto-darkening lens.

Another aspect relates to a remote control for an auto-darkening lens including a mode selector to select an operational mode of an auto-darkening lens, and a value selector to adjust the selected operational mode.

Another aspect relates to a method of operating an auto-darkening lens including using a wireless remote control providing control inputs to an auto-darkening lens to adjust at least one operating mode thereof.

Another aspect relates to a method of making an auto-darkening lens including preparing circuitry for operating a controllable light shutter of an auto-darkening lens, said preparing including preparing a receiver to receive wireless signals from a wireless remote control to adjust operation of such controllable shutter.

Another aspect relates to an auto-darkening lens system including an auto-darkening lens, including a controllable light shutter, operating circuitry to control light transmitting characteristics of the controllable light shutter, and a heads-up display to provide information concerning the auto-darkening lens in the area of the controllable light shutter of the auto-darkening lens.

The present invention is useful for eye protection by an automatically darkening light shutter in a helmet or goggle assembly or in another device, if desired. The switching mechanism for powering the light shutter on and off or for selecting operational characteristics may be an integral part of the light shutter or frame assembly or other component or portion thereof.

According to an aspect of the invention, an indicator system for a head mountable apparatus includes a number of indicators, an input to provide selective inputs to the indicators to cause the indicators to provide output indications, the indicators being in the peripheral field of view of a wearer of such head mountable apparatus in ordinary use, the indicators being located relative to each other, whereby the indications provided thereby may be comprehended based on at least one of relative location to each other and location in such head mountable apparatus. The indicators also or alternatively may be provided in a remote control unit.

Another aspect relates to a protective apparatus for at least a portion of the face of a wearer, including a protective shield positionable with respect to the face of a wearer, a viewing area to permit viewing through the shield, and a number of indicators to indicate information to a wearer, the indicators being located at least one of relative to each other and to the shield to provide information to a wearer based on energization and location of such indicators; and/or the indicators may be included in a remote control unit.

Another aspect relates to a method of conveying information to a person wearing a shield device protecting at least part of the wearer's face, including selectively energizing one or more respective indicators in a remote control unit to convey information to the person.

These and other objects, features, advantages and functions of the invention will become more apparent as the following description proceeds.

It will be appreciated that although the invention is described with respect to one or more embodiments, the scope of the invention is limited only by the claims and equivalents thereof. It also will be appreciated that if the invention is described with respect to several embodiments, features of a given embodiment also may be used with one or more other embodiments.

Also, although the invention is described with respect to a welding shutter (also known as a light shutter) used in a welding helmet for eye protection therein and with respect to several other devices for eye and/or face protection, it will be appreciated that the various features of the invention may be used in conjunction with other devices and functions.

To the accomplishment of the foregoing and related ends, the invention, then, comprises the features hereinafter described in the specification and particularly pointed out in the claims, the following description and the annexed drawings setting forth in detail certain illustrative embodiments of the invention, these being indicative, however, of but several of the various ways in which the principles of the invention may be suitably employed.

BRIEF DESCRIPTION OF THE DRAWINGS

In the annexed drawings:

FIG. 3 is a side elevation view of an embodiment of auto-darkening lens with vertically oriented/spaced-apart indicators;

FIG. 4 is a back plan view of the auto-darkening lens of FIG. 3;

FIGS. 5 and 6 are, respectively, a side elevation view and a back plan view of an embodiment of auto-darkening lens with both horizontally/spaced-apart indicators and vertically/spaced-apart indicators;

FIG. 7 is a schematic side elevation view of an auto-darkening lens in a respirator, space helmet or the like;

and

Figure 10:
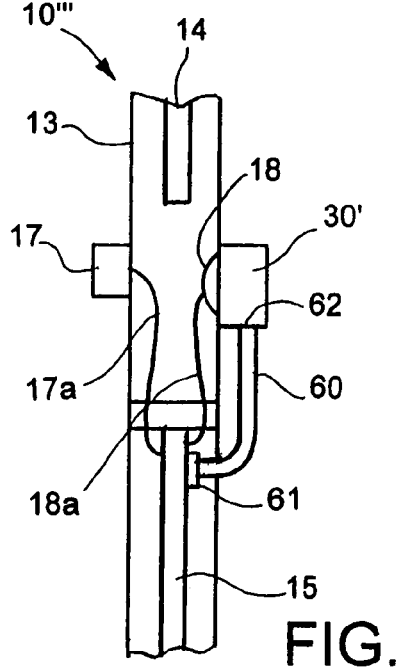
Figure 11:
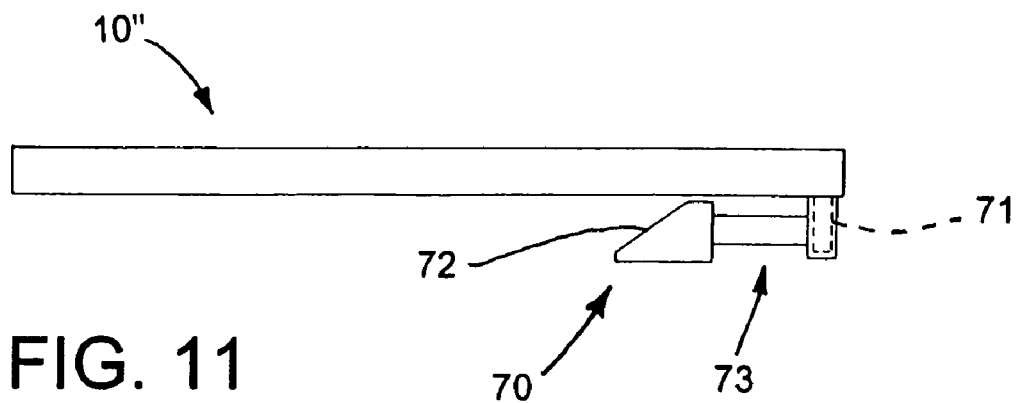
Figure 12:
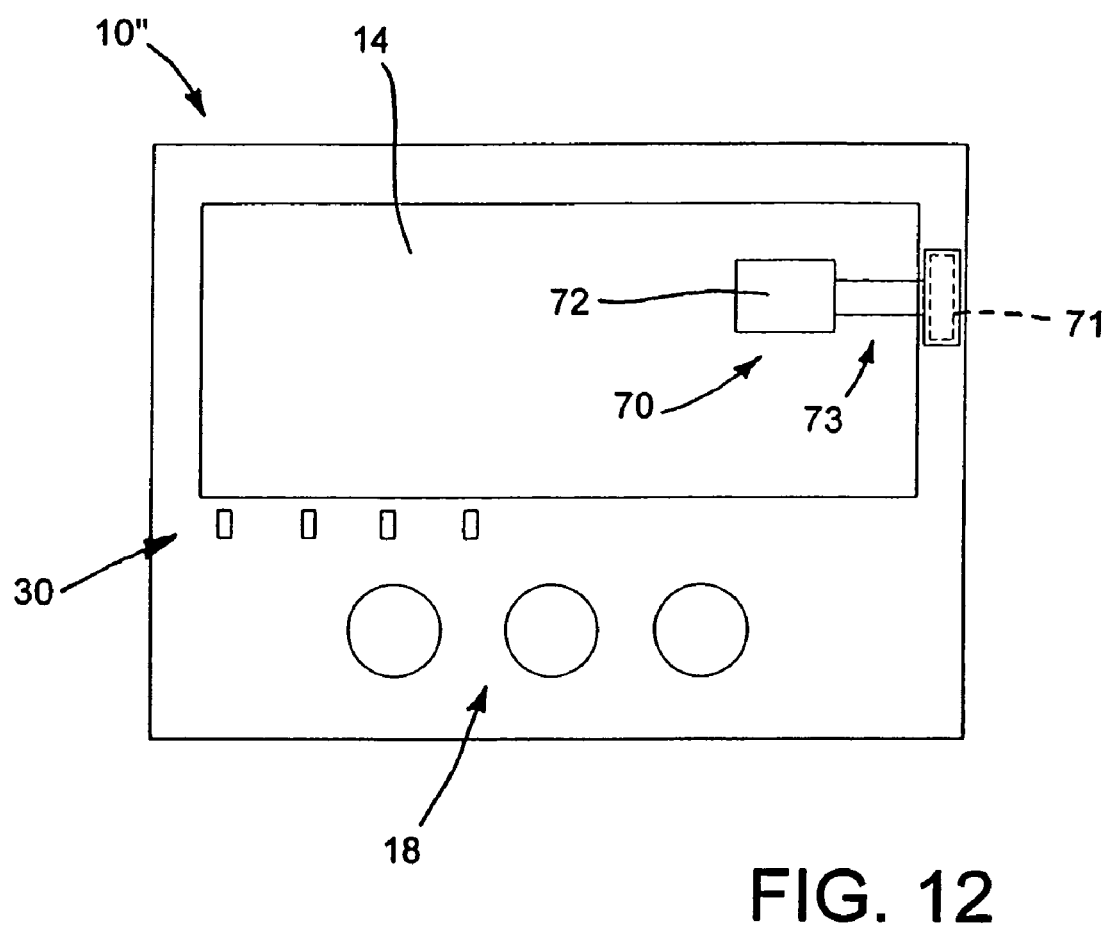
Figure 13:
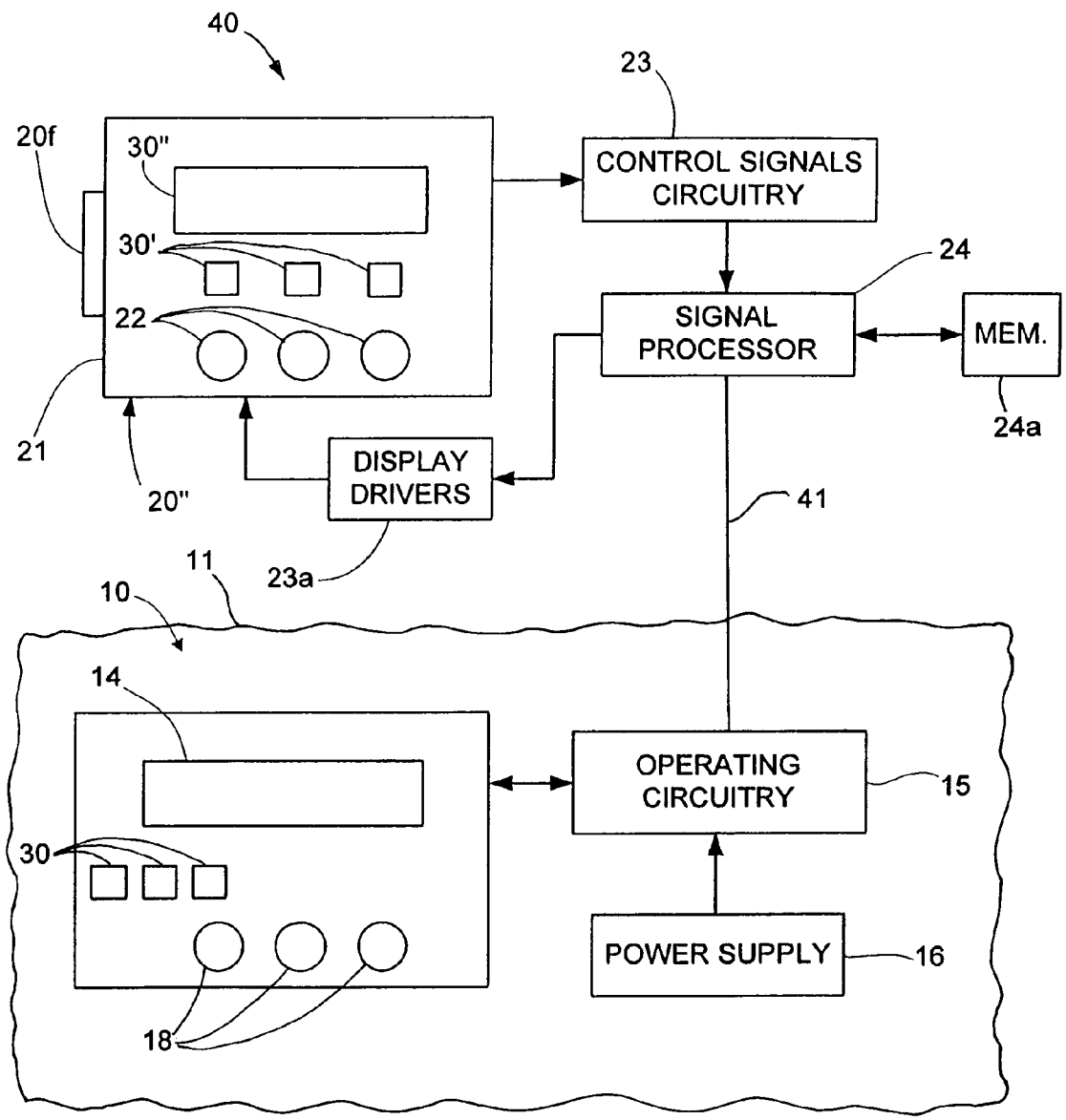

FIG. 10 is a schematic side elevation view of an auto-darkening lens with indicators that receive optical inputs;

FIGS. 11 and 12 are top and front schematic illustrations of an auto-darkening lens with a heads-up display; and FIG. 13 is a schematic illustration of a wired remote control with indicators and a display for an auto-darkening lens in a helmet.

DESCRIPTION

Figure 1A:
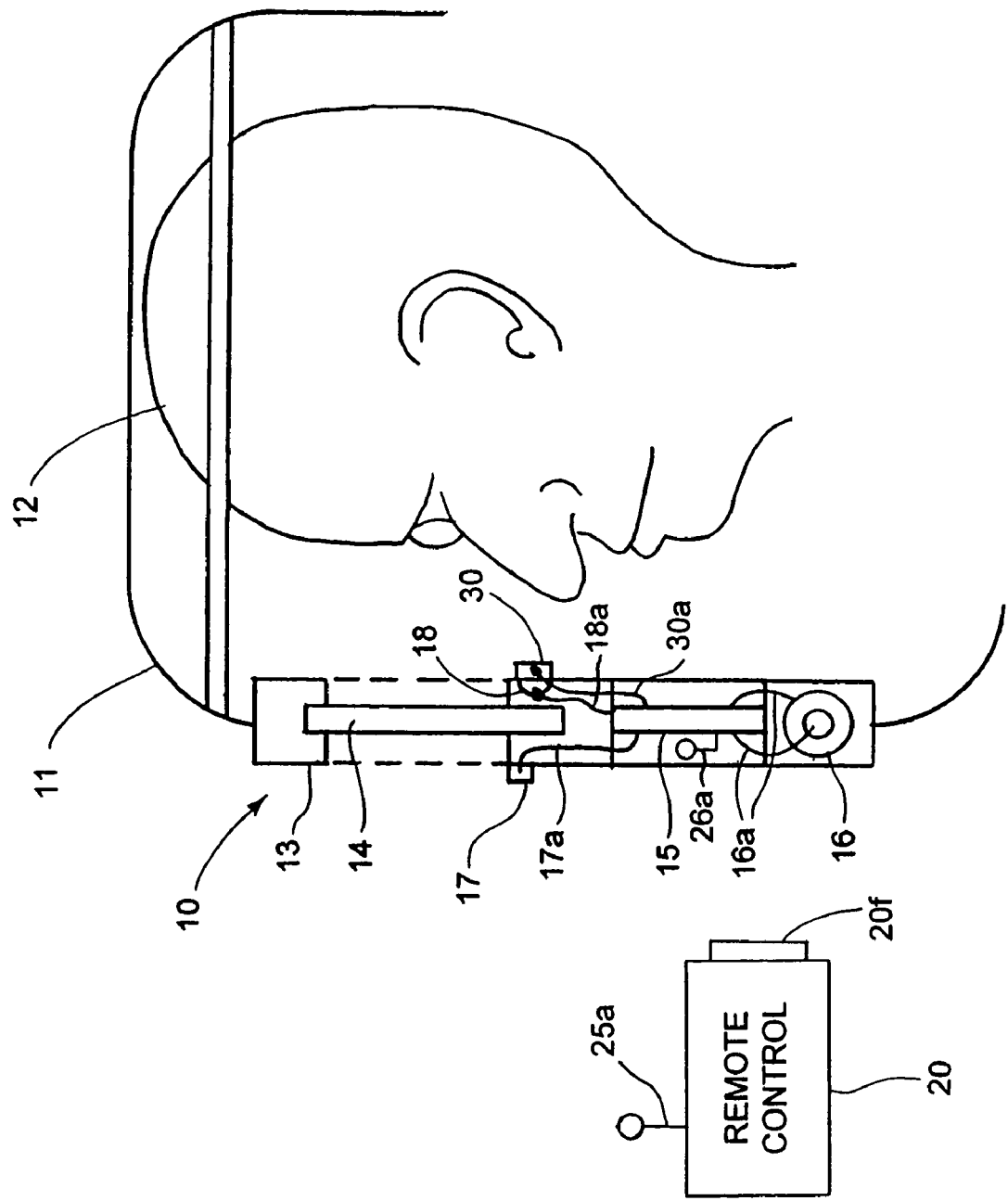
FIG. 1A is a schematic side elevation view, broken away, of an auto-darkening lens in a welding helmet in place on the head of a wearer.
Figure 1B:
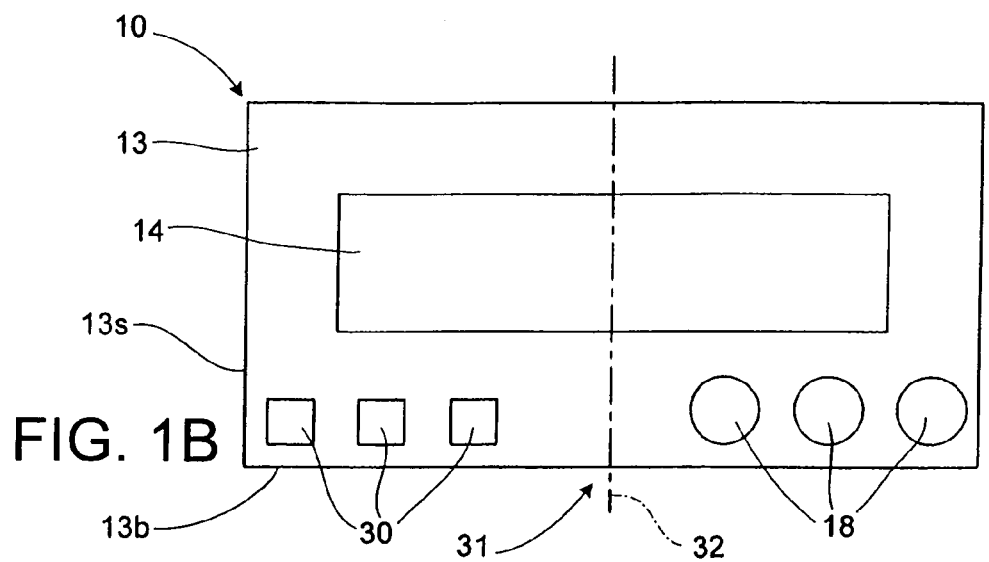
FIG. 1B is a back plan view of the auto-darkening lens of FIG. 1A illustrating horizontally oriented/spaced-apart indicators.

Referring now to the drawings, and initially to FIGS. 1A and 1B, an auto-darkening lens (sometimes referred to as ADL) 10 is illustrated in a welding helmet 11 in position on the head of a wearer 12 (sometimes referred to as a user). In the description below primed reference numerals are used to represent parts that are similar to parts that are designated by the same unprimed reference numeral. Reference to directions, such as horizontal, vertical, left, right, up, down, is for relative reference in the illustrated embodiments only and is not intended to be limiting. The drawings are not necessarily to scale.

The auto-darkening lens 10 includes, for example, a support structure or housing 13, a variable light transmission shutter 14 mounted with respect to the support structure, operating circuitry 15 and a power supply 16. Connections 16a couple the power supply 16 to provide power to the operating circuitry 15. Associated with the operating circuitry 15 is a photosensor 17, which is coupled to the operating circuitry by connections 17a, to sense occurrence of or a condition requiring a need for the auto-darkening lens 10 to darken or to lighten, e.g., to decrease light transmission during welding or to increase light transmission in the absence of welding. The operating circuitry 15 operates the auto-darkening lens to various conditions of light transmission. Several control buttons and switches schematically shown at 18 in FIGS. 1A and 1B are coupled by connections 18a to the operating circuitry 15 and may be operated by the wearer 12 to turn on the operating circuitry 15 to operate the shutter 14, e.g., to adjust the desired degree of shade (shade number), to set a delay time, to set sensitivity, etc. As an example, the switches 18 may be membrane switches. The operating circuitry 15, power supply 16, photosensor 17, and buttons and switches 18 may be mounted on, in or part on and part in the support structure or may be otherwise located, as may be desired.

In use of the auto-darkening lens 10 in the welding helmet 11, a wearer 12 may turn on the power and set the desired dark shade of the shutter 14 by using the buttons and switches 18. The wearer then puts the welding helmet 11 on the head with the shutter in front of the eyes for viewing work. The shutter 14 may be in its relatively clear or high light transmission condition (or state) to allow the wearer to view the work; and upon sensing occurrence of welding, the photosensor 17 indicates the same to the operating circuitry to cause the shutter to assume a dark or relatively reduced light transmission condition (or state). When welding ceases, the operating circuitry allows the shutter to return to the relatively clear condition.

Figure 2A:
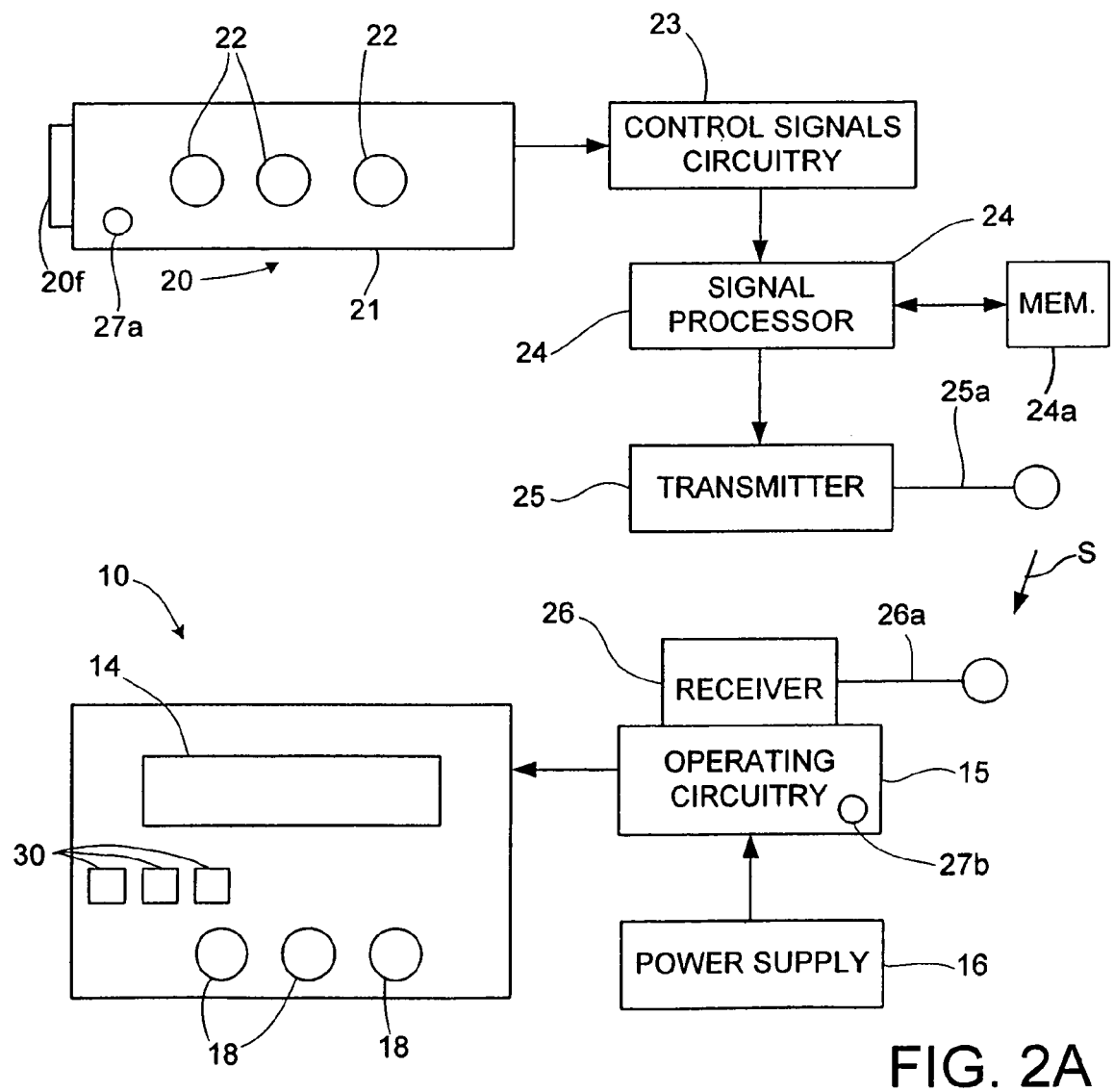
FIG. 2A is a schematic illustration of a remote control system associated with the welding helmet or other system that uses an auto-darkening lens.
Figure 7:
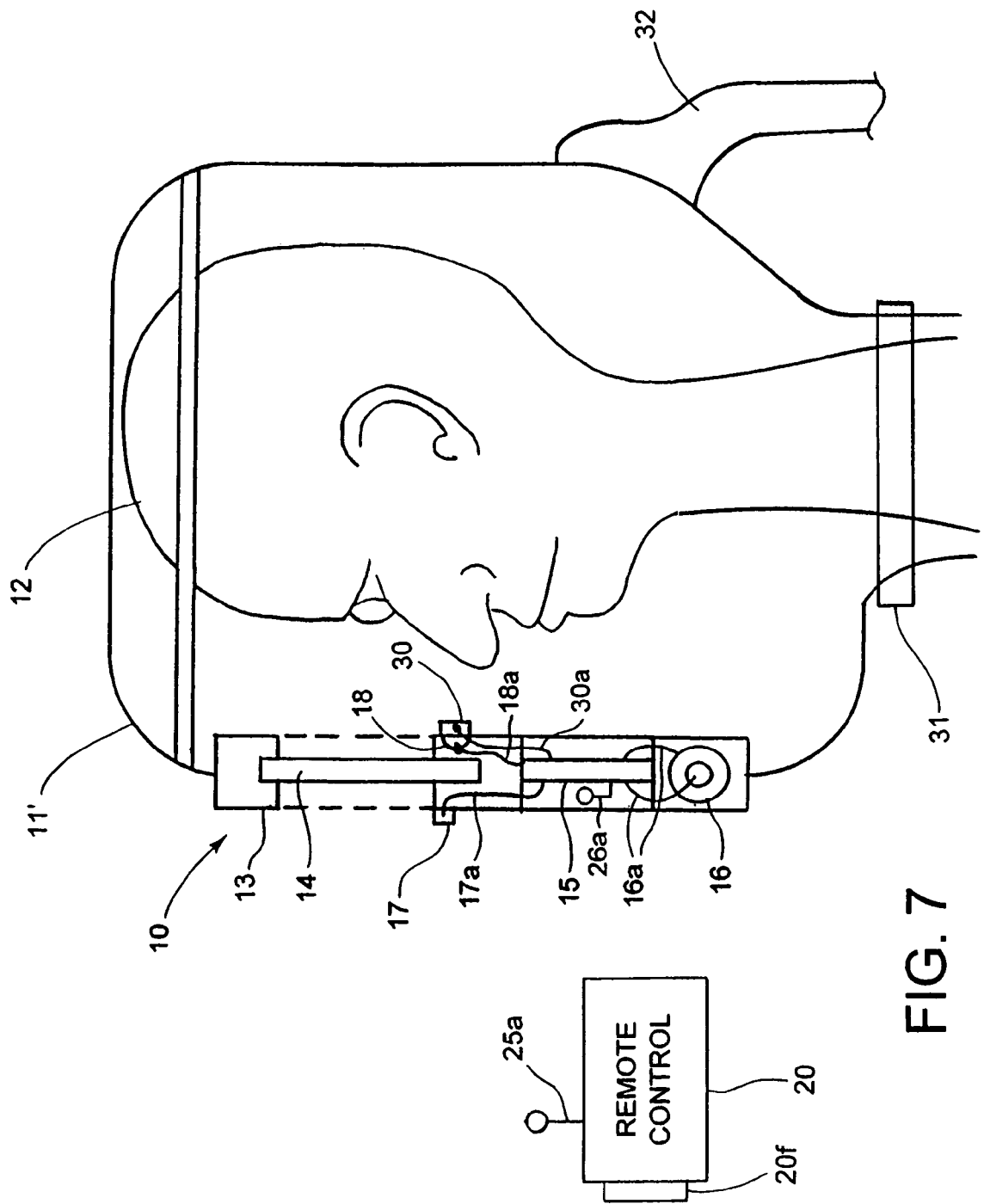

In FIG. 2A a remote control 20 for the system that uses the auto-darkening lens 10 is illustrated. Such system may be the welding helmet 10 of FIGS. 1A and 1B or may be a respirator helmet as is illustrated in FIG. 7; such system may be some other device that uses an auto-darkening lens of the various types described herein or other devices.

The remote control 20 includes a control unit 21 that may have controls 22. For example, the controls 22 may include one or more buttons, switches, control knobs, etc., e.g., membrane switches or other input devices, that can be operated by a user, e.g., pressed, turned, etc., to cause a desired operation of the auto-darkening lens, e.g., via the operating circuitry 15.

The remote control 20 may be portable as to be hand held; it may be placed on a table or other surface. It may be carried in a pocket of the user or attached to the outside of the system, e.g., welding helmet, with which it is used. Such attachment may be relatively permanent or it may be temporary allowing for removal when desired, e.g., being attached by a snap fastener, Velcro type fastener, or other fastener to the helmet or to the clothing, etc., of the user. As examples, the remote control 20 may be attached to a side of a welding helmet 11 or to clothing of a user, to a glove, to a wrist band on a user, etc. An exemplary fastener is represented at 20f.

The remote control 20 includes control signals circuitry 23 to deliver for use by the operating circuitry 15 control signals representative of the operating of one or more of the controls 22 by a user. A signal processor 24 may provide inputs to a transmitter device 25 associated with the remote control 20 that transmits signals received from the signal processor 25 to provide inputs to the operating circuitry 15. The inputs from the signal processor 14 provided to the transmitter device 25 represent settings, inputs, adjustments, etc., of the controls 22. The signal processor 24 may provide appropriate signal level boosting or attenuation, coding or decoding, and/or other functions to provide the transmitter device with signals that may be transmitted as a representation of the settings of the controls 22. In an example, the controls 22 may include two buttons that can be pressed by a user, e.g., even while wearing work gloves, to provide signals to the control signals circuitry 23. For example, one button could be a mode selector, e.g., to select the operating parameter or mode that is to be adjusted., e.g., shade number, sensitivity, delay, etc., of the auto-darkening lens 10; and the other button may select a value for a selected mode function or parameter by cycling through the possible settings for that mode or parameter in response to pressing the respective button.

The transmitter device 25 may be a wireless device, such as a radio frequency (rf) transmitter; it may be an infrared, ultraviolet, or other optical unit or an audio or ultrasonic unit, etc., being able to transmit signals using various transmitting techniques. The effective transmission range of the transmitter device 25 may be as selected by the manufacturer. In an example, the effective transmission range of the transmitter device 25 may be relatively short, e.g., on the order of a few feet. As an example, the range may be from about 6 inches to about 2 feet, e.g., approximately in the range of movement of the hand or arm of a user, so signals from the remote control 20 will affect the local auto-darkening lens 10, e.g., reach a receiver in the operating circuitry 15 of the auto-darkening lens, on the one hand, and will not affect another auto-darkening lens system of a nearby user. One example of such a remote control 20 may be of the type that is used conventionally in the automotive industry, e.g., an rf device that sends an rf signal to unlock or to lock vehicle door locks; and, as is described below, a receiver associated in the operating circuitry 15 receives such rf signal and carries out the function(s) and/or adjustments represented by such signals. As is the case for such automotive remote control, the present invention may use an encoded security feature to avoid one user affecting the auto-darkening lens of another user; such encoding may be achieved by using respective frequencies, by using a specific code word preceding a control word, or by some other hardware, software or other mechanism, etc.

The operating circuitry 15 includes a receiver device 26 for communication with the transmitter device 25. The receiver device 26 may receive inputs from the remote control 20 transmitter device 25 to effect the desired adjustments of the operating circuitry 15 by the user and, thus, the desired operation of the auto-darkening lens 10. The receiver device 26 may be a part of the operating circuitry and may have an rf antenna 26a or other device for receiving signals from an antenna 25a (or other signal transmitting device, e.g., optical, audio, etc.) associated with the remote control 20 transmitter device 25. Such signal transmission is represented by arrow S in FIG. 2A.

As the cost of including the receiver device 26 and associated encoding and/or decoding circuitry as a part of the operating circuitry 15 ordinarily would not be expected to be particularly expensive, it is possible to include the receiver device 26 and such circuitry as a usual portion of the operating circuitry 15 and, thus, of the auto-darkening lens 10. Therefore, in the future, if a user desires to employ a remote control 20 with the auto-darkening lens 10 and the system with which it is used, the user only may have to acquire a remote control that is suitably able to communicate with the receiver device 26 of the system.

In using the remote control 20, a user may make various adjustments to a welding helmet 11 (or other system that uses an auto-darkening lens), e.g., using controls 18 to set shade number, sensitivity, etc.; and then the user may put on the welding helmet. For example, if ambient or other conditions change or for some other reason causing a desirability to change shade number or sensitivity, etc., the user can make adjustments to the controls 22 of the remote control 20. Those adjustments are transmitted by the transmitter device 25 to the receiver device 26 in the operating circuitry 15 or associated with the operating circuitry of the auto-darkening lens 10 to provide desired operation of the auto-darkening lens. The operating circuitry 15 may include circuitry that allows the remote control adjustments and the adjustments that may be directly on the auto-darkening lens or helmet, etc., to operate redundantly or, in a sense, in parallel. For example, the control last set, or adjustment last made, e.g., by the controls 18 or 22, may be detected and be the control that determines the most current adjustment of the auto-darkening lens 10. Alternatively, one or more switches 27a, 27b, which respectively are connected in the circuitry of the remote control 20 and operating circuitry 15, may be operated to provide an indication to the operating circuitry, for example, of which of the controls 18, 22 would dominate or determine operation of the operating circuitry and auto-darkening lens 10.

If desired, the controls 18, for example, that are shown built in the auto-darkening lens 10 support housing and/or in the welding helmet 11 may be omitted or disabled to allow adjustments to be provided only by the remote control 20.

If desired, the signal processor 24 and/or the transmitter device 25 may include a memory 24a, for example. The settings or adjustments by the controls 22 may be processed, e.g., decoded or put into an appropriate format to determine what operation of the controls by the user would represent; and in such case the remote control 20 may be used to set operation of the controllable shutter 14 of the auto-darkening lens 10. As a non-limiting example, the memory may have data representing signals that would have to be sent to the operating circuitry 15 to obtain a given shade; and that shade may be set by the user adjusting a respective control 22, for example.

The auto-darkening lens 10 also is shown in FIG. 2A, as part of a welding helmet 11, and includes a controllable shutter 14, controls 18, and indicators 30. These are discussed further below.

Indicators 30 indicate operating conditions of the auto-darkening lens 10. The indicators 30 may be coupled, as at 30a (FIG. 1A), to the operating circuitry or to some other device that operates the indicators. Examples of operating conditions may include, without limitation, the current shade or light transmitting condition of the shutter 14, e.g., is it clear or dark; reserve power supply power level, e.g., how much charge remains in the power supply (such as a battery) before becoming unable to supply adequate power to the operating circuitry 15 to operate the shutter 14; whether power from an external source is connected for operating the auto-darkening lens; whether the auto-darkening lens 10 is on, e.g., is receiving power to the operating circuitry 15; what shade level has been set, e.g., by the buttons and switches (controls) 18; what delay time and/or sensitivity has been set, e.g., by the buttons and switches 18; etc. The remote control 20 also may be used to provide such control inputs, as is elsewhere described herein.

Figure 2B:
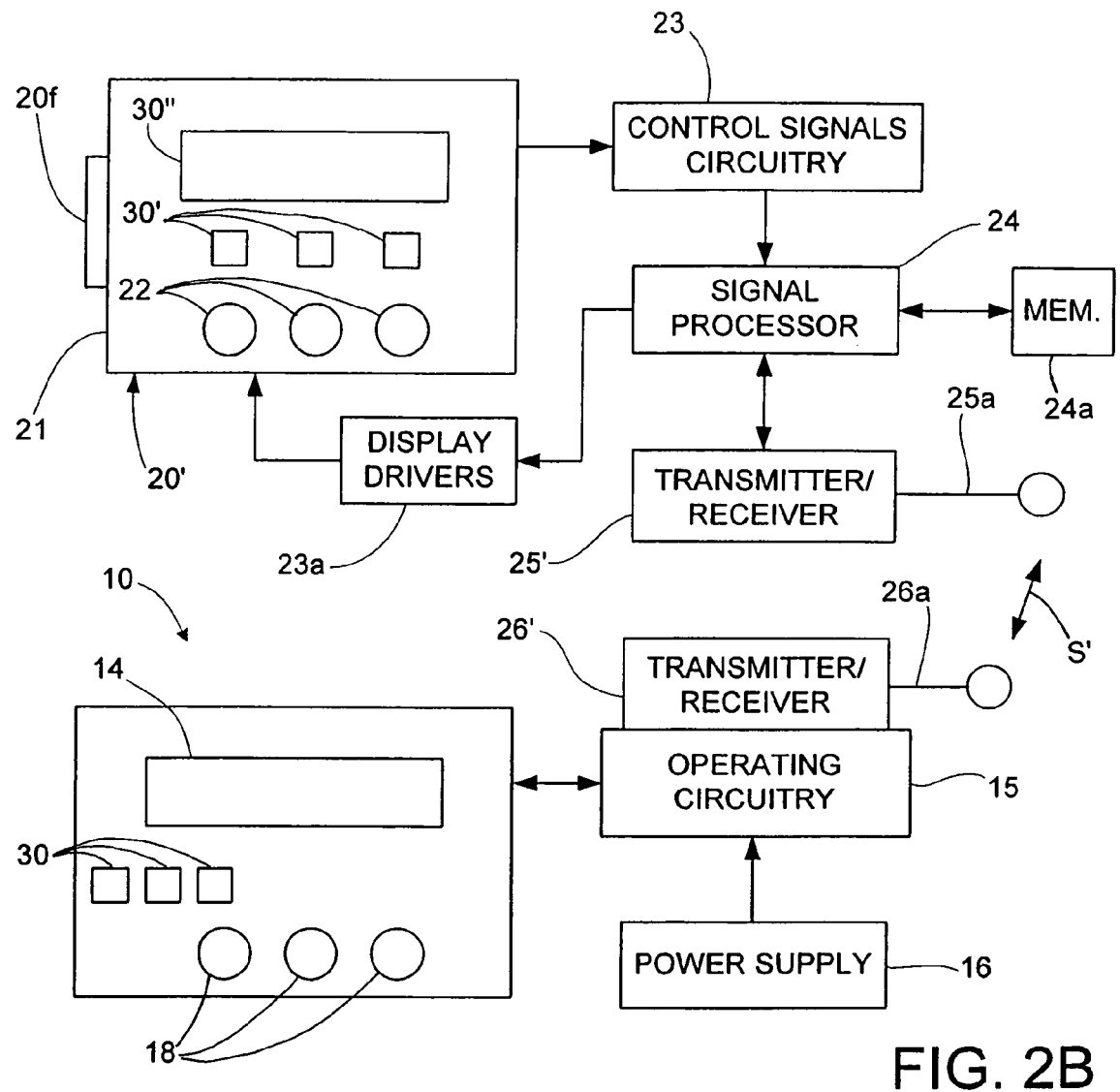
FIG. 2B is a schematic illustration of a remote control system associated with the welding helmet or other system that uses an auto-darkening lens.

Briefly referring to FIG. 2B, another remote control 20' is illustrated. The remote control 20' includes a number of indicators 30' and a display 30". The indicators 30' may be similar to the indicators 30, e.g., light emitting diodes or some other device to indicate operation of the remote control 20' and/or of the auto-darkening lens 10. The display may be, for example, an alphanumeric display to convey information to the user in addition to or in place of the information provided by the indicators 30'. An example display 30" is a liquid crystal display. In addition to the control signal circuitry 23, the remote control 20' includes display driver circuitry 23a that drives the respective indicators 30' and display 30" to provide appropriate outputs. In the remote control device 20' a transmitter/receiver device 25' includes both a transmitter device, as in the transmitter device 25', and a receiver portion that receives signals. In the operating circuitry 15' or associated with the operating circuitry 15' is a receiver/transmitter 26' that receives signals, as does the receiver device 26, and also transmits signals to the transmitter/receiver device 25'. Signal transmission is represented by the arrow S' in FIG. 2B. The signal processor 24' may include capability both to provide to the transmitter/receiver device 25' signals representing adjustments by the controls 22 for transmitting to the auto-darkening lens 10 and to receive via the transmitter/receiver device 25' signals from the receiver/transmitter device 26' to operate the display driver circuitry 23a to operate the indicators 30' and/or display 30".

Referring back to FIGS. 1A and 1B, the indicators 30 may be of the type that provide a light output. For example, each indicator may be a light emitting diode, an organic light emitting diode, an incandescent bulb, a combination of a light source and a light modulating device, such as a liquid crystal light modulator, or other type of device that provides a light output or indication based on light in response to an appropriate energization. The light output may be the generating or emitting of light by a given light source or it may be modulation of the light from a light source. The light output may be white, may be of a given color, or may be of different respective colors.

Operation of the indicators 30 may be provided by the operating circuitry 15. For example, the operating circuitry may provide respective signals and, if needed, power to cause respective indicators to provide a light output, to modulate light from a light source, to provide respective colors of light, etc. Such respective signals from the operating circuitry 15 may indicate the above-mentioned operating conditions of the auto-darkening lens 10 or other information that may be of interest, useful or needed by the wearer 12.

Location of the indicators 30 is such that they would generally be in the peripheral field of view of the wearer 12 when the wearer is wearing the auto-darkening lens in a usual operative position with respect to the eyes of the wearer 12 and the wearer is looking through the shutter 14. The indicators 30 may be mounted on the support structure or housing 13 or may be mounted elsewhere, provided in use with the auto-darkening lens 10 in place before the eyes of the wearer 12, the indicators generally are, in the peripheral field of view of the wearer. With the auto-darkening lens 10 before the eyes of the wearer, the indicators 30 would be so close to the face of the wearer that it would be difficult, if not impossible, for the wearer to focus an eye on the indicators as to see them clearly with good focus.

As is illustrated in FIGS. 1A and 1B, the indicators 30 are at the bottom of the auto-darkening lens 10 and are mounted on the support structure 13; and the indicators are arranged in a row to the left side 31 of approximate center, e.g., vertical centerline 32, of the auto-darkening lens. Other orientations are possible, examples of which are described below.

In the illustrated embodiment of FIGS. 1A and 1B the indicators 30 are located to only one side of the centerline 32. Locating the indicators only on one side of the centerline 32 helps to avoid confusion as to which of the indicator (or indicators) is illuminated. Since the nose of the wearer tends to separate at least part of the peripheral views of the respective eyes of the wearer, locating the indicators 30 on only one side of the centerline 32, which ordinarily lines up approximately with the nose of the wearer, tends to have such indicators seen only by one eye of the wearer. By locating the indicators 30 as described, then even without directly viewing them in focus by an eye of the wearer the relative positions of respective indicators usually can be discerned. Also, the angle at which the indicator(s) 30 is seen by the wearer can help the wearer to discern which indicator(s) is energized and, thus, convey information to the wearer. Therefore, information can be conveyed to the wearer by the indicators 30 based on the relative location of the energized (or not energized) indicator(s) in the peripheral field of view, based on the relative location of an indicator to other indicators, and based on the angle at which the indicator(s) is seen in the peripheral field of view.

Having the indicators on both sides of the centerline 32 may tend to cause confusion as to information being conveyed. However, the indicators may be at both sides of the viewing window, e.g., the sides of the shutter 14, and in such case ordinarily the indicator(s) at only one side at a time would be active to provide a light output, for example, so as to avoid possible apparent superimposition problems and confusion to the wearer.

It is possible to provide distinguishing features to one or more of the indicators, such as color, intensity, flashing/not flashing, etc.

Depending on the proximity of the indicators 30 to the face of the wearer 12, the indicators may be closer or further from the eyes of the wearer. For example, the indicators may be relatively close to the ordinary field of view if they are located relatively close to the face of the wearer; and they may be relatively further from the ordinary field of view if they are located relatively far from the ordinary field of view of the wearer. Therefore, if the indicators 30 are mounted on the support structure 13 and the auto-darkening lens 10 usually is worn close to the face and eyes of the wearer 12, the indicators 30 may be relatively close to the shutter 14; but if the auto-darkening lens usually is worn relatively further from the face and eyes of the wearer, the indicators could be positioned relatively further away from the shutter.

Energization of the indicators 30 may be effected by inputs from the operating circuitry 15, as was mentioned above. For example, the operating circuitry may include a monitor to detect the amount of power (power reserve) remaining in a battery power supply for the auto-darkening lens; and in response to that detection the operating circuitry may illuminate a given indicator 30 or several indicators to indicate there is adequate power, the amount of power, e.g., the amount of time left before power runs out, that power will run out shortly, etc. If the power were to run out shortly, it would be desirable for the wearer to plan to stop working, e.g., welding, shortly and in any event before the power runs out, thereby to avoid the possibility that the work would be continued while the eyes would be unprotected by the dark state of the shutter 14. The operating circuitry 15 may provide an input to one or several indicators to indicate the pre-set shade level to which the shutter 14 will be operated when it is in the dark state, or to indicate response speed of the shutter, sensitivity level of the shutter, e.g., sensitivity of the photosensor 17 and operating circuitry to cause the shutter to be operated in the dark condition. The operating circuitry 15 may provide an input to one or several indicators to indicate that the shutter 14 is in a clear state condition or a dark state condition; this is valuable information because sometimes it is not possible for the wearer to recognize the condition of the shutter 14 by only looking through the shutter.

It will be appreciated that the operating circuitry 15 may have suitable detectors, operating software or firmware, and components, etc., to be able to determine which signals are to be directed to which indicators 30 to effect energization of such indicator(s). The operating software or firmware may be written and the particular components of the operating circuitry 15 may be constructed by a person or persons having ordinary skill in the art based on the description herein. Moreover, as is described in the above-referenced and incorporated patents, various auto-darkening lenses and control systems are shown, and the present invention may be used, if desired, therewith.

While the auto-darkening lens 10 is worn, e.g., as part of a helmet 11, the indicators 30 generally may be observed by a wearer in the peripheral field of view of the wearer. As a wearer looks out through the shutter 14 toward work, such as an item being welded, brazed, glued, sanded, etc. in an industrial environment, or a dentist looks into the mouth of a patient, or a surgeon looks closely at an internal organ of a patient undergoing surgery, the indicators 30 generally may be seen in the peripheral field of view outside the ordinary direct field of view that the wearer intends to have in focus, e.g., while carrying out work in the focused field of view.

The indicators 30 may be the same so they provide the same color light output. The indicators 30 may be different. Differences may be such that the indicators are different sizes and/or shapes, produce different color light, different intensities of light, produce blinking (at respective frequencies) or no blinking, etc. The indicators may be aligned in a single horizontal row, e.g., parallel to the bottom edge 13b of the support 13, as is illustrated in FIG. 1B; or the indicators may be at different locations. Each individual indicator may be one color light or a given indicator may be capable of providing different color light output, e.g., by using several closely positioned light emitting diodes that provide different color light or by using selective filters that can be turned on/off in response to energization, as a liquid crystal filter type device, for example. The indicators 30 may be operated to flash or not, depending on information they are to convey to the wearer 12.

While the auto-darkening lens 10 is not in position in use on the head before the eyes of a wearer, the indicators 30 also may be seen by looking at them. In such case the indicators may be adequately far from the eyes of a person viewing them that the indicators may be seen in focus by the viewer's eyes. The indicators 30 may be used to provide information to a person who is adjusting the buttons and switches 18 indicating the settings made by such adjustments. Therefore, the indicators 30 may be used to provide valuable information both while in use before the eyes of the wearer and while not on the head of the wearer.

It will be appreciated that although the indicators 30 are illustrated and described as mounted on the support or housing 13, of the auto-darkening lens 10, the indicators may be positioned elsewhere. As an example, the indicators may be mounted on the welding helmet 11 itself.

Turning to FIGS. 3 and 4, an embodiment of auto-darkening lens 10' in which the indicators 30 are in a vertically oriented/spaced apart relation is shown. The indicators 30 are aligned in a column at the left side edge 13s of the auto-darkening lens 10' adjacent the shutter 14 and are outside the usual field of view through the shutter while generally being in the peripheral field of view of the wearer to the left side of the head of the wearer. The auto-darkening lens 10' may be otherwise the same as the auto-darkening lens 10. Operation of the auto-darkening lens 10' may be the same as or similar to that described above for the auto-darkening lens 10.

If desired, the indicators 30 may be located both at a side edge and bottom edge of the shutter 14, e.g., on the support structure 13 side edge 13s and bottom edge 13b, as is illustrated schematically for an auto-darkening lens 10" in FIGS. 5 and 6.

Referring to FIG. 7, a respirator 30 is illustrated schematically. The respirator 30 includes an auto-darkening lens 10 (or 10' or 10") mounted in a helmet structure 11' that fully encloses the head of a wearer and may be sealed to the neck of the wearer at 31 or may be part of an overall enclosure, such as a diving suit, space suit, or other suit typically used for entering hazardous environments. One or more tubes 32 provide air flow and, if desired, provide for exhausting the products of breathing with respect to the interior of the helmet structure 11'. The use and operation of the indicators 30 for the auto-darkening lens 10 in the respirator 30, etc., may be the same as is described above. If desired, a separate remote control schematically illustrated at 33 may be coupled by wire, radio signals, etc., to the operating circuitry 15 to allow the wearer of the respirator 30 and auto-darkening lens 10 to adjust the operative conditions, settings, etc., of the auto-darkening lens by manual or other operation of the wearer. Since it would be difficult and sometimes inadvisable for the wearer briefly to remove the auto-darkening lens 10 and respirator 30 to make such adjustments while wearing the respirator, the ability to make adjustments to settings of the auto-darkening lens 10 remotely may be advantageous. Furthermore, being able to discern the settings being made by remote control, perhaps by another person, as the user discerns the indicators 30 in the user's peripheral field of view, allows the user to confirm that proper settings are being made.

From the just described use of the indicators in a respirator or the like, it will be appreciated that the invention allows a wearer of the auto-darkening lens to discern meaningful operational, settings, etc., or other information even if the wearer is able to look directly at the indicators 30 but cannot obtain a focused view of the indicators, e.g., because the indicators are too close to the eyes.

Figure 8:
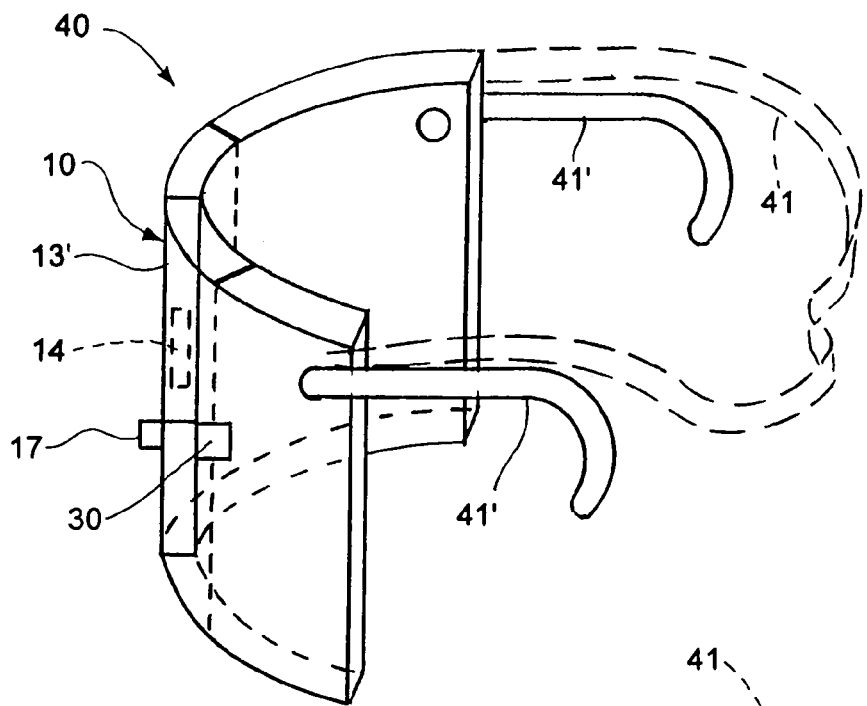
FIG. 8 is a schematic side elevation view of an auto-darkening lens in a dental shield face mask.

Briefly referring to FIG. 8, an auto-darkening lens 10 (or 10' or 10") is illustrated in a dental mask or face protector 40. The dental mask 40 may be clear plastic or other material or it may have a light blocking characteristic. With the auto-darkening lens 10, for example, mounted in the dental mask 40, e.g., to a support structure 13' thereof, and the dental mask 40 mounted on the head of a dentist, e.g., being held in place by a strap 41 or temple pieces 41' so as place the mask and the auto-darkening lens 10 in front of the face, the shutter 14 of the auto-darkening lens may be operated to protect the eyes of a dentist or dental technician from bright light and/or from light of a particular wavelength or wavelengths, e.g., ultraviolet used to cure a dental material, that might otherwise be harmful to the eyes, while the shutter still allows viewing therethrough absent such bright or possibly harmful light. The face protector 40 and the auto-darkening lens 10 also protect the face from particulates, fluids, etc. during dental procedures. Similarly, the dental mask 40 with the auto-darkening lens 10, for example, may be used by a surgeon conducting surgery, an industrial worker carrying out various tasks, and for other purposes, etc., to provide similar utility would be provided for a dentist.

Figure 9:
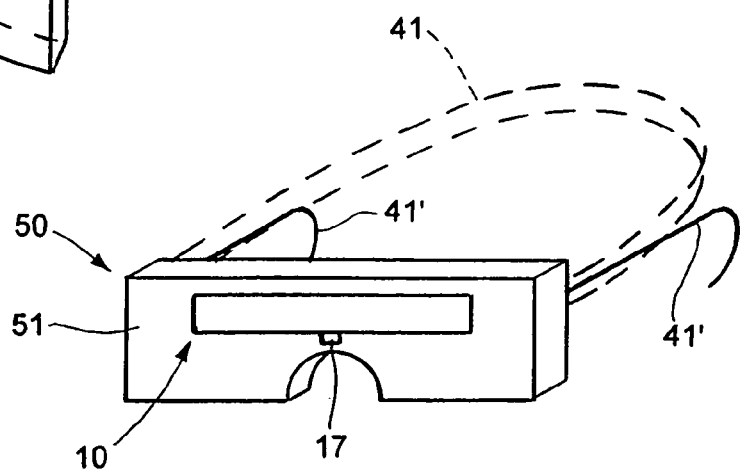
FIG. 9 is a schematic side elevation view of an auto-darkening lens in goggles.

Briefly referring to FIG. 9, the auto-darkening lens 10 (or 10' or 10") is shown in goggles 50. The goggles may be used for many different purposes, such as for protection in industrial environments, for racing automobiles or airplanes in an open cockpit, for observing experiments or other conditions in which bright light, even nuclear flash, may occur, etc. The goggles include a support structure 51, sometimes referred to as a frame with appropriate components, as is schematically illustrated in FIG. 8, to allow the goggles to be worn on the head of a person. The auto-darkening lens may be mounted in such a support structure for use generally as was described above.

The goggles 50 may be in the form of eyeglasses that can be worn by a wearer. Such eyeglasses would include a support structure, such as a lens holder of an eyeglass frame, temple pieces to hold to the ears of a wearer, etc. as is schematically illustrated in FIG. 9. The eyeglasses 50 may use a lens 10 (or 10' or 10") that is a safety lens, which has a characteristic capable of meeting industrial standards of safety glasses for eye protection in an industrial plant.

Briefly referring to FIG. 10, an embodiment of auto-darkening lens 10''' that is similar to the other auto-darkening lenses 10, 10' and 10" is illustrated. The indicators 30' of the auto-darkening lens 10''' receive light from respective light conducting members, e.g., light pipes, fiber optic members, reflectors, etc., which are schematically illustrated at 60. A light input 61 to respective light conducting members 60 is provided from a source in the auto-darkening lens 10''', for example, from light emitting diodes or other devices on or associated with the operating circuitry 15, e.g., such light emitting devices may be mounted on a circuit board of the operating circuitry. The indicators 30' may be the light output end 62 of the respective light conducting members 60; or the light conducting members may provide light input to respective indicators to cause such indicators to provide a light output able to be seen by the wearer/user 12 (FIG. 1A). The indicators 30' are positioned with respect to the auto-darkening lens 10''' in a manner the same or similar as the indicators 30 that are described above.

Turning briefly to FIGS. 11 and 12 an auto-darkening lens 10" is illustrated with a heads-up display. The auto-darkening lens 10" is similar to the auto-darkening lens 10 described above; except the auto-darkening lens 10' includes a heads-up display 70. The heads-up display 70 provides to a user information concerning settings of the auto-darkening lens and/or other information. The operating circuitry 15 includes circuitry to provide information, e.g., alphanumeric information, for displaying to the user via the heads-up display 70. Such circuitry for displaying information via the heads-up display 70 may be conventional circuitry, e.g., that provides a shade number representative of the shade number setting of the auto-darkening lens, or some other information for viewing by the user. The heads-up display 70 may be a conventional heads-up display of the type that includes a display device 71, e.g., a liquid crystal display or some other display, appropriate reflectors 72 and/or lenses, and a housing 73 containing the foregoing to provide an image that is able to be directed, e.g., by reflection, to the user's eye.

Briefly turning to FIG. 13, a wired remote control 20" for use with an auto-darkening lens 10 of a welding helmet 11 is illustrated as a welding helmet system 40. The wired remote control 20" is connected by a wire 41 to the operating circuitry 15 of the auto-darkening lens 10. The wired remote control 20" operates in a manner similar to the wireless remote control 20', which is described above with respect to FIG. 2B. The wired remote control 20" may be held in the hand, placed on a belt or other garment worn by a user, placed on the welding helmet 11, or placed at some other location. If desired, the wired remote control 20" may be removed from any of such locations for use to make various adjustments and/or to provide a display or indication of information to the user or may be used without removing it.

The wired remote control 20" includes a number of controls 22 that may be operated by the user or by some other individual. The wired remote control 20" also includes a number of indicators 30' and, if desired, a display 30" that can display to the user or to some other individual information pertaining to the auto-darkening lens 10, such as that information mentioned above and/or other information.

The auto-darkening lens 10 also includes controls 18 and indicators 30, and these may be used to provide the operating and indicating functions described above, for example.

The wired connection 41 electrically connects the wired remote control 20" and the operating circuitry 15. The wired connection 41 allows the wired remote control 20" to provide control signals to the auto-darkening lens 10 via the operating circuitry 15 in the manner described above, for example, or in another suitable way. The wired connection 41 also provides information from the auto-darkening lens 10 to the wired remote control 20", for example, to provide information via the indicators 30' and/or display 30" pertaining to operating conditions of the auto-darkening lens 10 or some other information, as may be desired. Thus, it will be appreciated that the welding helmet system 40 uses the wired remote control 20" to control operation of the auto-darkening lens 10, which may display indications using the indicators 30 to represent settings and/or operating conditions of the auto-darkening lens 10, and also to provide information to the user via the indicators 30' and display 30" without the need for the auto-darkening lens 10 to be removed from a use position or location.

INDUSTRIAL APPLICATION

The remote control of the present invention provides for remote adjustment of an auto-darkening lens and also may provide indications or information pertaining to operation or settings of the auto-darkening lens. The auto-darkening lens may be used in a number of devices, several examples of which are described above and other devices, too.

The invention claimed is:
1. An auto-darkening lens system, comprising
an auto-darkening lens, including a controllable light shutter capable of attenuating light to the eyes of a user over a range of shades while the auto-darkening lens is worn by the user,
operating circuitry to control light transmitting characteristics of the controllable light shutter over such range of shades, a wireless remote control in proximity to and operable by the user of the auto-darkening lens to adjust at least one operating parameter of the auto-darkening lens including the shade of the auto-darkening lens, and further comprising indicators adapted to display to the user while the auto-darkening lens is worn by the user information pertaining to operation of the auto-darkening lens, said indicators being in position relative to the auto-darkening lens for conveying such information in the peripheral field of view of the user.

2. The auto-darkening lens system of claim 1, said remote control comprising a wireless remote control having a security feature to tend to prevent adjustment of an unintended auto-darkening lens.

3. The auto-darkening lens system of claim 1, said wireless remote control comprising a transmitter having a range limited to on the order of from about 6 inches to about 2 feet.

4. The auto-darkening lens system of claim 1, said operating circuitry including a receiver.

5. The auto-darkening lens system of claim 1, said auto-darkening lens including controls to adjust at least one operating parameter of thereof.

6. The auto-darkening lens system of claim 5, wherein the remote control provides redundant adjustment of such at least one operating parameter.

7. The auto-darkening lens system of claim 6, further comprising a switch for determining priority of control between the remote control and the controls of the auto-darkening lens.

8. The auto-darkening lens system of claim 1, further comprising a memory to store data to coordinate settings input by the remote control with operational parameters of the auto-darkening lens.

9. The auto-darkening lens system of claim 1, further comprising an attachment to attach the remote control to at least part of the auto-darkening lens.

10. The auto-darkening lens system of claim 1, further comprising an attachment device for attaching the remote control to a support.

11. The auto-darkening lens system of claim 1 further comprising an attachment device to attach the remote control to another object, said attachment device comprising a Velcro type fastener.

12. The auto-darkening lens system of claim 1, further comprising a helmet, the auto-darkening lens being mounted in the helmet, and the remote control being external of the helmet.

13. The auto-darkening lens system of claim 12, said remote control having a wireless radio frequency (rf) connection to provide input to the operating circuitry.

14. The auto-darkening lens system of claim 13, said remote control having a transmission range limited to on the order of from less than one foot to several feet.

15. The auto-darkening lens system of claim 14, said remote control having a transmission range limited to on the order of from about 6 inches to about 2 feet.

16. The auto-darkening lens system of claim 1, further comprising a respirator helmet, the auto-darkening lens being mounted in the respirator helmet.

17. The auto-darkening lens system of claim 1, further a face mask, the auto-darkening lens being mounted in the face mask.

18. The auto-darkening lens system of claim 1, further comprising a face shield, the auto-darkening lens being mounted in the face shield.

19. The auto-darkening lens system of claim 1, further comprising a dental mask, the auto-darkening lens being mounted in the dental mask.

20. The auto-darkening lens system of claim 1, said auto-darkening lens comprising safety eye glasses.

21. The auto-darkening lens system of claim 1, said auto-darkening lens comprising goggles.

22. The auto-darkening lens system of claim 1, said auto-darkening lens comprising eye glasses.

23. The auto-darkening lens system of claim 1, said remote control comprising a display.

24. The auto-darkening lens system of claim 1, said remote control comprising a display having a number of indicators similar to the indicators that are in position relative to the auto-darkening lens.

25. The auto-darkening lens system of claim 1, further comprising a heads-up display adapted to provide useful information in the field of view of a user concerning the auto-darkening lens while the user performs useful tasks wearing the auto-darkening lens system.

26. An auto-darkening lens system, comprising
an auto-darkening lens, including a controllable light shutter capable of attenuating light over a range of shades to provide such light to the eyes of a user wearing the auto-darkening lens,
operating circuitry to control light transmitting characteristics of the controllable light shutter over at least part of such range of shades,
a wired remote control to adjust at least one operating parameter of the auto-darkening lens via the operating circuitry while the auto-darkening lens system is worn,
the wired remote control including indicators to indicate at least one of a setting and an operating condition of at least one of the auto-darkening lens and operating circuitry the indicators being viewable through the auto-darkening lens in the direct field of view of a user wearing the auto-darkening lens.

27. The auto-darkening lens system of claim 26, said auto-darkening lens including controls to adjust at least one operating parameter of thereof.

28. The auto-darkening lens system of claim 27, wherein the remote control provides redundant adjustment of such at least one operating parameter.

29. The auto-darkening lens system of claim 27, further comprising a switch for determining priority of control between the remote control and the controls of the auto-darkening lens.

30. The auto-darkening lens system of claim 26, further comprising a memory to store data to coordinate settings input by the remote control with operational parameters of the auto-darkening lens.

31. The auto-darkening lens system of claim 26, further comprising a helmet, the auto-darkening lens being mounted in the helmet, and the remote control being external of the helmet.

32. The auto-darkening lens system of claim 26, further comprising indicators adapted to display to a user while the auto-darkening lens is worn by the user information pertaining to operation of the auto-darkening lens, said display comprising indicators for conveying quantitative information in the peripheral field of view of the user.

33. An auto-darkening lens system, comprising
an auto-darkening tens, including a controllable light shutter, operating circuitry to control light transmitting characteristics of the controllable light shutter over a range of shades while the auto-darkening lens is worn by a user, and a heads-up display to provide in the direct field of view of a user wearing the controllable light shutter information concerning the auto-darkening lens, the heads-up display comprising a display and an optical system for directing light from the display of the heads-up display to at least one eye of a user.

34. The auto-darkening lens system of claim 33, further comprising a housing for the heads-up display.

35. The auto-darkening lens system of claim 34, further comprising lenses in the housing.

36. The auto-darkening lens system of claim 33, further comprising a helmet, the heads-up display being in the helmet.

37. The auto-darkening lens system of claim 33, further comprising a reflector to direct information from the heads-up display to a user.

38. The auto-darkening lens system of claim 37, wherein the optical system is adapted to direct light from the display of the heads-up display to only one eye of a user.

39. The auto-darkening lens system of claim 37, the heads-up display comprising an alphanumeric display.

40. An auto-darkening apparatus for protection of the eyes of a user from incident electromagnetic energy, comprising a controllable variable electromagnetic energy transmission lens positionable before at least one eye of a user while the user is wearing the lens, a control circuit adapted to control transmission of electromagnetic energy through said lens over a range of shades, a remote control adapted to adjust operation of said control circuit and/or said lens permitting a user to effect such control while wearing the lens, and an indicator adapted to indicate in the peripheral field of view of a user wearing the lens at least one operational parameter of the lens while the lens is being worn by the user, whereby while the lens is being worn by a user, adjustments may be made to effect control of said control circuit and/or said lens and the results of such adjustments may be displayed to the user by the indicator to the user.

41. The auto-darkening apparatus of claim 40, wherein the remote control is wireless.

42. The auto-darkening apparatus of claim 40, wherein the remote control is wired to the control circuit.

43. The auto-darkening apparatus of claim 40, wherein the indicator is positioned relative to the lens to provide information in the peripheral field of view of a user wearing the lens indicative of the operational shade characteristic of the lens.

* * * * *

UNITED STATES PATENT AND TRADEMARK OFFICE
CERTIFICATE OF CORRECTION

| | |
|---|---|
| PATENT NO. | : 7,342,210 B2 |
| APPLICATION NO. | : 10/898297 |
| DATED | : March 11, 2008 |
| INVENTOR(S) | : Fergason |

It is certified that error appears in the above-identified patent and that said Letters Patent is hereby corrected as shown below:

Column 18, line 66, replace "tens" with --lens--.

Signed and Sealed this

Seventeenth Day of June, 2008

JON W. DUDAS
*Director of the United States Patent and Trademark Office*